(12) United States Patent
Annergren et al.

(10) Patent No.: US 6,465,710 B1
(45) Date of Patent: Oct. 15, 2002

(54) ABSORBENT STRUCTURE WITH IMPROVED ABSORPTION PROPERTIES

(75) Inventors: Jeanette Annergren, Mölnlycke; Lars WÅgberg, Sundsvall, both of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/284,635

(22) PCT Filed: Oct. 17, 1997

(86) PCT No.: PCT/SE97/01739

§ 371 (c)(1),
(2), (4) Date: Aug. 10, 1999

(87) PCT Pub. No.: WO98/18504

PCT Pub. Date: May 7, 1998

(30) Foreign Application Priority Data

Oct. 28, 1996 (SE) ............................................... 9603920

(51) Int. Cl.[7] .............................................. A61F 13/15
(52) U.S. Cl. .................. 604/368; 604/375; 604/378
(58) Field of Search ................................ 604/358, 378, 604/367, 370, 376, 375, 374, 379, 385.01, 385.23, 368

(56) References Cited

U.S. PATENT DOCUMENTS

| | | | | |
|---|---|---|---|---|
| 4,699,619 A | * | 10/1987 | Bernardin | 604/378 |
| 4,699,823 A | * | 10/1987 | Kellenberger et al. | 428/219 |
| 4,718,899 A | * | 1/1988 | Itoh et al. | 604/368 |
| 4,826,497 A | * | 5/1989 | Marcus et al. | 604/359 |
| 5,432,215 A | * | 7/1995 | Girg et al. | 524/28 |
| 5,573,994 A | * | 11/1996 | Kabra et al. | 502/402 |
| 5,855,572 A | * | 1/1999 | Schmidt | 604/378 |

FOREIGN PATENT DOCUMENTS

| | | |
|---|---|---|
| EP | 0 202 125 B1 | 11/1986 |
| EP | 0 343 931 A2 | 11/1989 |
| EP | 0 693 508 A1 | 1/1996 |
| EP | 0 603 508 B1 | 5/1998 |

\* cited by examiner

*Primary Examiner*—Dennis Ruhl
*Assistant Examiner*—Jamisue Webb
(74) *Attorney, Agent, or Firm*—Burns, Doane, Swecker & Mathis, LLP

(57) ABSTRACT

The invention pertains to an absorbent structure (3) in an absorbent article such as a diaper (100), an incontinence protector, a sanitary napkin or the like, which structure exhibits two end portions (8, 9) and a crotch portion (6) located therebetween, wherein the absorbent structure (3) comprises superabsorbent material having a thermo-reversible liquid absorption capacity. The superabsorbent material having a thermo-reversible liquid absorption capacity is located in one or several delimited regions in the absorbent structure (3).

15 Claims, 2 Drawing Sheets

ABSORBENT STRUCTURE WITH IMPROVED ABSORPTION PROPERTIES

TECHNICAL FIELD

The present invention pertains to an absorbent structure in an absorbent article such as a diaper, an incontinence protector, a sanitary napkin or the like, which structure exhibits two end portions and a crotch portion located therebetween, wherein the absorbent structure comprises superabsorbent material having a thermo-reversible liquid absorption capacity.

BACKGROUND OF THE INVENTION

In current absorbent articles such as diapers, sanitary napkins or the like, only approximately 60% of the total liquid absorption capacity of the absorbent body is utilized. Therefore, it has long been a wish to be able to increase the degree of utilization of the absorption capacity in the absorbent body.

An absorbent body of an absorbent article exhibits two end portions, and a crotch portion located therebetween. The crotch portion is the part of the diaper which is intended to be arranged at the narrowest region between the thighs of the user during use, and is the area of the diaper which is expected to be wetted by excreted body fluid first. Since the area which the liquid reaches first is constituted by a relatively limited area of the total absorbent structure, this implies that the area is rapidly saturated with liquid. Therefore, it is important that the liquid rapidly can be distributed from this area to the remaining parts of the absorbent structure. However, a small portion of the liquid always remains within the area around the wetting site, without being able to be distributed further to the remaining parts of the absorbent structure. Therefore, it is of great significance that the area of the absorbent structure which initially is wetted has the ability to retain the liquid which is not distributed out into the absorbent structure, so that rewetting, i.e. passage of liquid back out from the article, is avoided.

In order to obtain high absorption capacity in an absorbent body, absorbent articles of the above-mentioned sort usually contain superabsorbent materials. Superabsorbents are polymers with the ability to absorb liquid in a quantity many times their own weight. Furthermore, they have the ability to retain absorbed liquid even when they are subjected to an external pressure. The efficiency of such superabsorbents is dependent on many factors, such as where and how the superabsorbent is mixed into the absorbent body, which physical form the superabsorbent has, and physical and chemical properties such as absorption rate, gel strength, and liquid retention.

A phenomenon which is referred to as gel-blocking may negatively affect the absorption capacity of a fibre structure containing superabsorbents. Gel-blocking means that the superabsorbent forms a gel during wetting which blocks the pores in the fibre structure and thereby renders the transport of liquid from the wetting area to the remainder of the absorbent body difficult. This results in a poor utilization of the total absorption capacity of the absorbent body and, furthermore, results in an increased risk of leakage.

In order to increase the degree of utilization of the total capacity of the absorbent structure, and in order to prevent gel-blocking, the absorbent structure usually exhibits a number of layers with mutually different properties with regard to, among other things, absorption rate, liquid distribution and liquid retention.

For instance, it is previously known through EP 0,202,125 to have a lower content of superabsorbent material in an upper liquid receiving layer of an absorbent body, i.e. a layer intended to be facing a user, than in a lower part of the absorbent body. Accordingly, the liquid passes through the receiving layer without being absorbed by this and is brought further downwards in the absorbent structure. Thus, an advantage with this design is that the liquid is stored in the lower part of the absorbent body, which implies that the upper layer, closer to the user, substantially remains free from liquid. Another advantage of this previously known design is that the liquid also has time to be distributed from the wetting site out to the end portions of the article, since it takes a certain time for the liquid to reach the superabsorbent. This results in a higher utilization of the total liquid absorbing capacity of the absorbent article. However, a problem with such a design is that there is a risk that the upper absorbent structure is perceived as wet when repeated wettings occur, since it only has the ability-to retain a limited liquid quantity.

Furthermore, it is previously known through EP 0,343,941 to build up the absorbent body of three different layers, namely, a receiving layer, a liquid-distributing layer and a liquid-storing layer. The first layer, the receiving layer, consists of a hydrophillic structure with a wetting area which has a lower density than the remaining areas of the receiving layer. By means of this design of the absorbent body, with a more open structure having a lower density in the wetting area that in the remaining absorbent structure, a rapid liquid absorption of large liquid quantities is obtained within the wetting area. Thereafter, the liquid is distributed via the liquid-distributing layer and is absorbed by the liquid-storing bottom layer. With such a design of the absorbent body, it is true that a relatively rapid liquid admittance is obtained. On the other hand, the problem remains that the upper structure in the wetting area of the article has difficulty in retaining liquid when subjected to repeated wettings, something which results in increased rewetting and, accordingly, an increased risk of a wet surface closest to the user.

Still another disadvantage with the previously known absorbent structure is that it is complicated to manufacture since it consists of several different materials which have different densities in different portions.

SUMMARY OF THE INVENTION

However, by means of the present invention an absorbent structure of the sort mentioned in the introduction has been achieved, exhibiting a higher degree of utilization of the total liquid absorption capacity of the structure. By means of the invention an absorbent structure which exhibits an increased liquid-retaining ability in the wetting area of the article has also been achieved.

Furthermore, the risk of gel-blocking, with entailing impairment of the liquid distribution pattern and increased risk of leakage, is reduced by means of the invention.

According to the invention, this has been achieved by means of an absorbent structure comprising a superabsorbent material having a thermo-reversible liquid absorption capacity, located in one or several delimited areas in the absorbent structure.

According to a preferred embodiment, the superabsorbent material having a thermo-reversible liquid absorption capacity is primarily located in the crotch portion of the structure.

According to one embodiment, the thermo-reversible superabsorbent is constituted by a polymer, exhibiting a thermo-reversible liquid absorption capacity. A polymer which exhibits a thermo-reversible liquid absorption capacity is characterized in that the polymer changes geometrical configuration at a certain temperature, whereby the hydrophillic and hydrophobic groups of the polymer, respectively, take up another position, resulting in a substantial change of the liquid absorption capacity of the polymer. Accordingly, thermo-reversible polymers exhibit a cloud point at a certain temperature, $C_p$, at which the liquid absorption capacity of the polymer is changed. For those polymers which have been found to be suitable for the purpose, the cloud point $C_p$ occurs within the temperature interval 30–37° C., preferably within the temperature interval 32–35° C.

The liquid absorbtion capacity-of the intended polymers is lower at a temperature above 32–35° C., than at a temperature below 32–35° C. Since the body fluid initially has a temperature which is approximately 37° C., this implies that the body fluid, when reaching the absorbent structure, passes the thermo-reversible superabsorbent without being absorbed by it. The body fluid is distributed further on from the wetting site in the crotch portion of the diaper to the end portions of the absorbent structure, where the liquid is absorbed by conventional superabsorbent material, i.e. without thermo-reversible liquid absorption capacity. This results in an increased degree of utilization of the total absorption capacity of the absorbent body.

Thereafter, the thermo-reversible superabsorbent starts to swell when the body fluid has cooled down after a certain period of time to the cloud point of the superabsorbent, i.e. depending on the type of superabsorbent which is used, to a temperature around 32–35° C. Accordingly, this implies that the thermo-reversible superabsorbent can absorb the remaining liquid quantity within the crotch portion. In this manner, the risk that the article is perceived as being wet after a first wetting is eliminated.

A further advantage with a thermo-reversible superabsorbent which is located in the crotch area, or above all, in a portion of the crotch area in close connection to the wetting site of the absorbent structure, is that the risk of gel-blocking in this area is almost completely eliminated. The reason for this is that the greater part of the liquid already has been transported to other parts of the absorbent structure when the thermo-reversible superabsorbent starts to swell.

When a second wetting of the absorbent structure takes place, the temperature once again rises around the wetting site, which causes the liquid-containing thermo-reversible superabsorbent to be emptied of liquid. Thereafter, the liquid is distributed to the absorbent structure outside the crotch area, where the liquid primarily is absorbed by conventional superabsorbent material without thermo-reversible liquid absorption capacity. When the temperature of the liquid remaining in the crotch area after some time has cooled down to a temperature of around 32–35° C., the remaining liquid is absorbed by the thermo-reversible absorbent which is now emptied of liquid and therefore has the ability to swell once again. This ability to swell once more during the second wetting is of course also valid for subsequent wettings.

Since it takes some time before the liquid has cooled down to a temperature around 32–35° C., when using thermo-reversible polymers it is suitable that the remaining absorbent structure, i.e. the end portions, are built up from a certain portion of conventionally absorbing material which has the ability to momentarily absorb liquid and retain the liquid independently of temperature changes.

According to one embodiment, the thermo-reversible superabsorbent is constituted by a cross-linked co-polymer of N-isopropylacrylamide. This polymer is used, for example, in pharmaceuticals, in so-called drug-release systems in order to control the absorption of substances in the body. The compound is further described in EP 0,693,508 as being useful within a number of different fields, where absorption of a liquid is desirable. This polymer exhibits a low absorption of body fluid at a temperature above 32–35° C., while the absorption capacity is considerably higher when the temperature of the body fluid is below 32–35° C.

According to another embodiment, the thermo-reversible superabsorbent is constituted by a cross-linked co-polymer which is built up from N-isopropylacrylamide and a vinyl monomer containing carboxylic acid, such as acrylic acid. Since the carboxylic acid in the acrylic acid is hydrophillic and charged, the total absorption capacity of the superabsorbent is increased. Still another advantage of the carboxylic acid is that it assists in raising the temperature at which the thermo-reversible superabsorbent starts to absorb liquid, i.e. in raising the cloud point, $C_p$, of the polymer. However, this implies that it is of essential importance that the content of the vinyl monomer containing carboxylic acid is not too high in the thermo-reversible polymer. A further advantage of a low content of vinyl monomer containing carboxylic acid is that the salt sensitivity of the thermo-reversible superabsorbent is reduced.

According to a further embodiment, the thermo-reversible superabsorbent is constituted by a cross-linked co-polymer which is built up from N-isopropylacrylamide and a polymerizable monomer containing sulfonic acid, such as for example monomers of AMPS, i.e. 2-acryloamido-2methylpropane sulfonic acid. An advantage with monomers containing sulfonic acid is that sulfonic acid is a stronger acid than carboxylic acid, i.e. has a lower pKa-value than carboxylic acid.

According to a further embodiment, the thermo-reversible superabsorbent is constituted by a cross-linked cellulose derivative, such as for example ethylhydroxyethyl cellulose. An advantage with a superabsorbent which is constituted by a cellulose derivative is that the absorbent is manufactured from a renewable material. Another advantage with such a material is that it is biodegradable.

In order to further facilitate the distribution of the liquid from the wetting site to other portions, according to one embodiment the absorbent structure exhibits a first and a second layer, wherein the first layer which is intended to be closer to the user during use exhibits a lower density than the second layer. Consequently, a rapid initial liquid absorption ability is obtained in the first, more open layer, and an increased liquid wicking force is obtained to the finer capillaries in the second layer. It is also possible to increase the liquid distribution to the end portions of the absorbent body by providing a first layer with compression lines which extend along the longitudinal direction of the article. Since the finer capillaries in the compressed portions of the absorbent body transport the liquid better than the surrounding portions of the absorbent body, the initially wetted area is drained more rapidly of excreted body fluid.

The invention also includes absorbent articles such as sanitary napkins, diapers, incontinence protectors, or the like, comprising an absorbent structure enclosed in a cover, which structure comprises superabsorbent material having a thermo-reversible liquid absorption capacity primarily located in the crotch portion of the absorbent structure.

According to one embodiment of the absorbent article, the superabsorbent material having a thermo-reversible liquid absorption capacity is primarily located in the part of the crotch portion of the absorbent structure which is located closest to the liquid-permeable cover layer. An advantage with this embodiment is that the body fluid is distributed from the part of the absorbent structure which is located closer to the user during use to the part which is further away from the user. In this way, the risk of a wet surface in direct contact with the skin is reduced.

According to still another embodiment of the absorbent article, the absorbent structure comprises a liquid-receiving layer located closer to the liquid-permeable cover layer and a liquid storage layer located closer to the liquid-impervious cover layer. In this embodiment, the superabsorbent material having a thermo-reversible liquid absorption capacity is substantially located in the liquid-receiving layer of the absorbent structure.

BRIEF SUMMARY OF THE DRAWINGS

In the following, the invention will be described in greater detail with reference to the embodiments which are shown in the attached drawings.

DETAILED DESCRIPTION OF PREFERRED EMBODIMENTS

Figure 1:
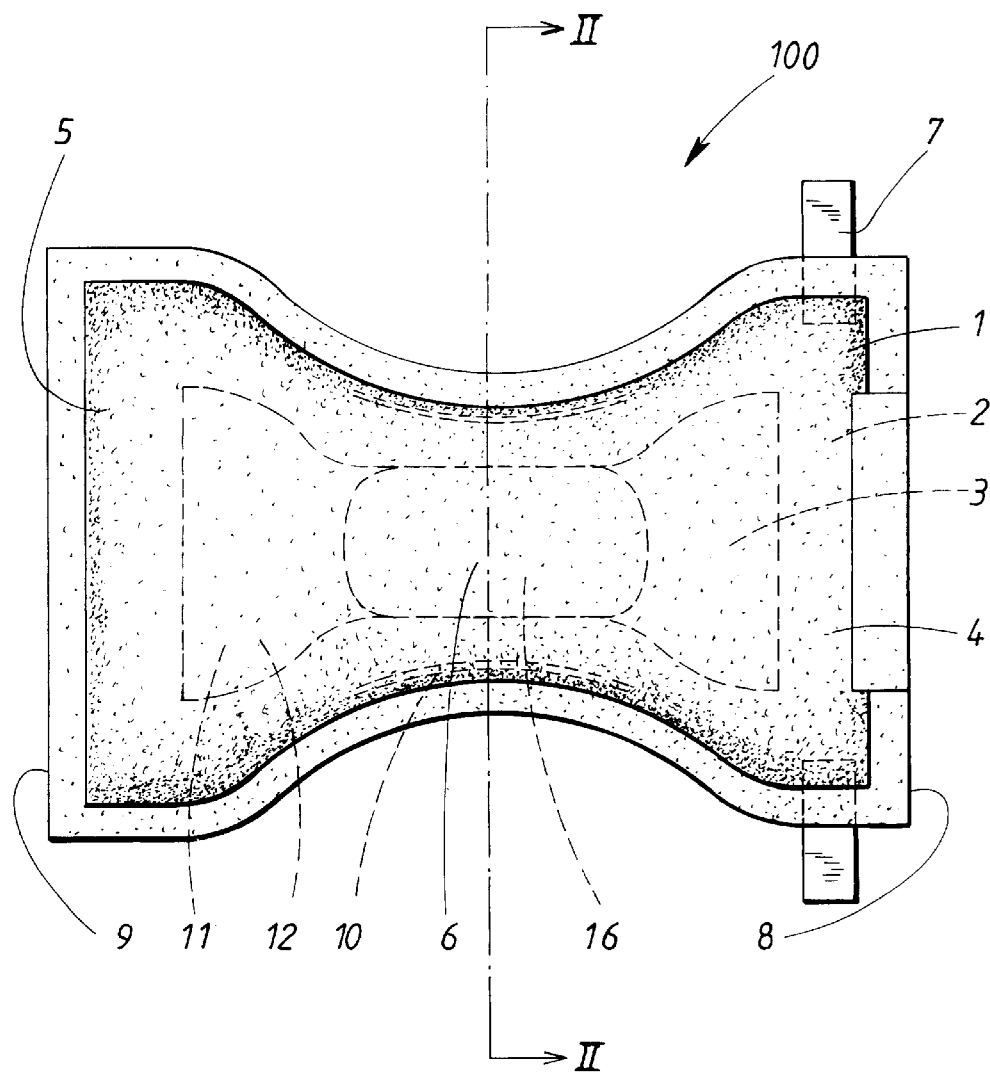
FIG. 1 shows a diaper according to the invention, seen from the side which is intended to be in contact with the user during use.

The diaper 100 shown in FIG. 1 comprises a liquid-permeable cover layer 1, for example of nonwoven fabric or perforated plastic film, a liquid-impervious cover layer 2, for example of plastic film or hydrophobic nonwoven fabric, and an absorbent body 3 enclosed between the cover layers 1, 2.

The diaper is intended to enclose the lower part of the torso of the user as a pair of absorbent pants. For this purpose, it is designed with two end portions 4, 5 and a crotch portion 6, located between the two end portions, which is intended to be applied in the crotch of the user between his/her legs during use. In order to make it possible to join the diaper together into the desired pant-shape, tape flaps 7 are arranged close to the rear waist edge 8 of the diaper. During use, the tape flaps 7 are attached to the front portion 5 of the diaper, close to the front waist edge 9, so that the diaper is kept together around the waist of the user.

Furthermore, the diaper according to FIG. 1 comprises pre-stretched elastic members 10, which may consist of elastic bands, thread-enclosed elastic threads, elastic foam or another suitable material. For reasons of simplicity, the elastic members 10 in FIG. 1 have been shown in an extended state. As soon as the stretching ceases, however, they will contract and form elastic leg cuffs on the diaper.

In the example shown in FIG. 1, the absorbent body 3 of the diaper is built up of two layers 11, 12, an upper liquid-receiving layer 11 and a lower liquid storage and distribution layer 12. The upper receiving layer 11 should be able to rapidly receive large liquid quantities during a short time, i.e. to have a high instantaneous liquid absorption capacity, while the lower storage and distribution layer 12 should exhibit a high liquid distribution ability and be able to drain liquid from the receiving layer 11 and distribute this in the storage and distribution layer 12. The differences in properties between the two layers 11 and 12 may be achieved by means of differences in density, whereby a fibre structure which is more strongly compressed distributes the liquid better than a corresponding fibre structure having a lower density, which by means of its large pore size has a higher instantaneous liquid absorption capacity and smaller wicking ability. Differences in absorption properties between the two layers may also be achieved by means of different fibre structures with different properties. Accordingly, cellulose fluff pulp manufactured in a chemical way exhibits higher liquid distribution ability as compared to, for example, pulp manufactured in a mechanical or chemi-thermomechanical way, so-called CTMP. A fibre structure containing cellulose fibres stiffened in a chemical way also exhibits a higher instantaneous liquid absorption capacity, but lower distribution ability than conventional chemical pulp. Other suitable materials for use as receiving layers 11 may be a wadding of synthetic or natural fibres or a fluffy nonwoven material.

In and around the wetting area 16 of the diaper, i.e. the area of the diaper which is expected to be hit by excreted body fluid first and which primarily is located in the crotch area 6 of the diaper and generally is somewhat displaced in a direction towards the front portion 5 of the diaper, a thermo-reversible superabsorbent is mixed into the layers 11 and 12 of the absorbent body 3.

The content of thermo-reversible superabsorbent should be at least 5% of the total weight in a dry state of the absorbent structure in the crotch area. The thermo-reversible super absorbent in the crotch area 6 is based, for example, on cross-linked N-isopropylacrylamide or a co-polymer of N-isopropylacrylamide and a vinyl monomer containing carboxylic acid, such as acrylic acid. The thermo-reversible superabsorbent can also be based on a cross-linked co-polymer of N-isopropylacrylamide and a polymerizable monomer containing sulfonic acid, such as monomers of AMPS, i.e. 2-acryloamido-methylpropane sulfonic acid. This polymer swells and absorbs liquid at temperatures below 32–35° C. Consequently, the liquid absorption capacity of the polymer may be utilized first when the temperature of the body fluid has cooled down to 32–35° C. The thermo-reversible polymer can also be constituted by a cellulose derivative exhibiting thermo-reversible liquid absorption capacity, such as for example EHEC, i.e. ethylhydroxyethyl cellulose. Furthermore, other polymers exhibiting a change in liquid absorption capacity within the temperature interval 30–37° C. are of course also applicable as thermo-reversible superabsorbents in the crotch area of the absorbent structure.

The thermo-reversible superabsorbent is intended to absorb and retain any liquid which has remained in the layer 11 after this has been drained by the second distribution and storage layer. In this way, rewetting by remaining liquid is avoided. Furthermore, the fibre structure is emptied of liquid before subsequent wettings.

In this context, the expression superabsorbent should be given a relatively wide interpretation and should be regarded as including both superabsorbent grains as well as granules, flakes or short fibres.

Figure 2:
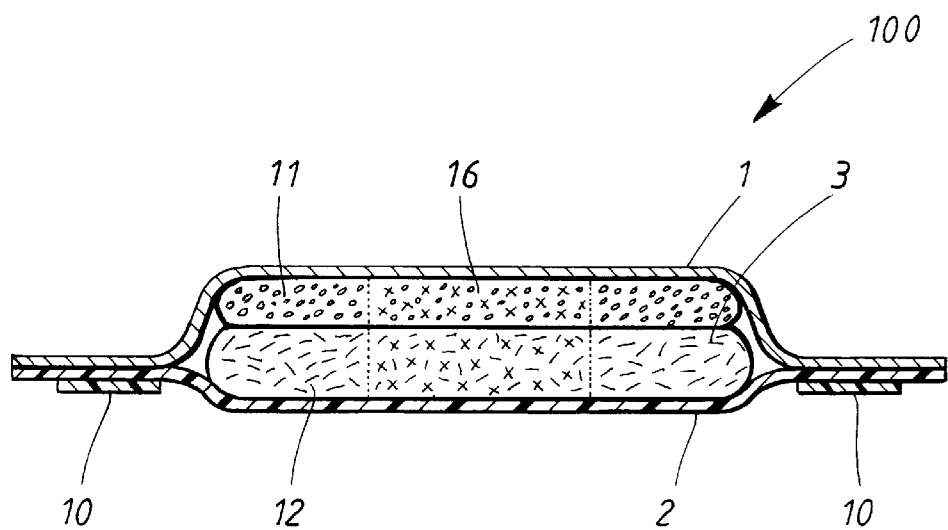
FIG. 2 shows a cross-section along the line II—II through the diaper shown in FIG. 1.
Figure 3:
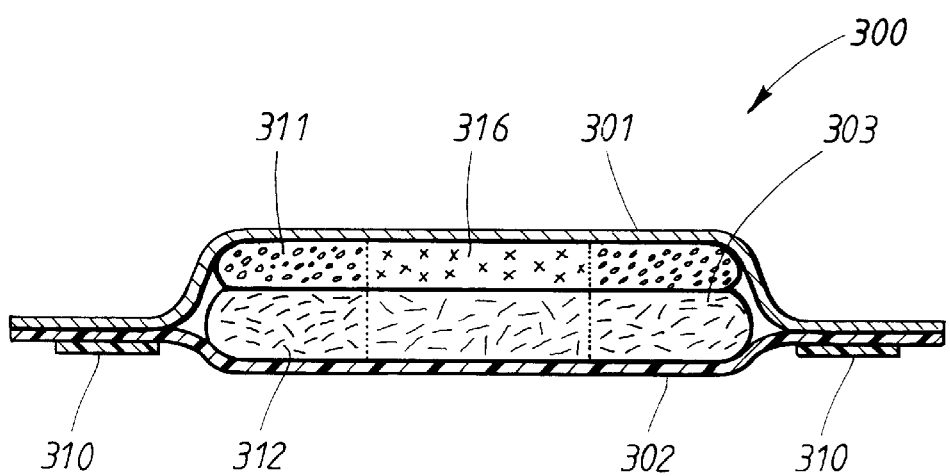
FIG. 3 shows a further cross-section through a diaper according to the invention.

The diaper 300 shown in FIG. 3 in cross-section has substantially the same fundamental structure as the diaper 100 in FIGS. 1 and 2. Accordingly, the diaper 301 exhibits an absorbent body 303 enclosed between the cover layers 301, 302. Furthermore, the absorbent body 303 consists of an upper liquid receiving layer 311, and an underlying liquid distribution and liquid storage layer 312. In and around the wetting area 316 of the diaper 301, i.e. the area of the diaper which is expected to be hit by excreted body fluid first, a thermo-reversible superabsorbent is mixed into the layer 311. The area of the layer 311 which contains a thermo-reversible superabsorbent, may also contain a certain portion of superabsorbent of a conventional type. In addition, the diaper 300 may comprise elastic members 310, which correspond to and have the same structure and function as elastic members 10 of diaper 100.

EXAMPLE 1

|  |  | Temp. (° C.) | 27° C. | 28° C. | 29° C. | 30° C. | 31° C. | 32° C. | 33° C. | 34° C. | 35° C. | 37° C. |
|---|---|---|---|---|---|---|---|---|---|---|---|---|
| Swelling | Sample 1 |  | 0 | 22.8 | 24.43 | 16.29 | 13.03 | 3.26 | 3.26 | 3.26 | 0 | 3.26 |
| (cm3/gram | Sample 2 |  | 26.32 | 24.68 | 23.03 | 18.1 | 13.16 | 4.94 | 4.94 | 4.94 | 0 | 4.94 |
| dry SAP) | Sample 3 |  | 23.27 | 19.94 | 19.94 | 13.29 | 11.63 | 4.99 | 3.32 | 0 | 0 | 0 |

EXAMPLE 1

Example 1 shows a table over liquid absorption, i.e. swelling of cross-linked polymer of N-isopropylacrylamide in a water solution. The cross-linked polymer of N-isopropylacrylamide is polymerized with a conventional cross-linking agent, such as methylenebisacryloamide. In practice, the trial is performed by adding 0.10 gram superabsorbent material comprising 10 weight-% N-isopropylacrylamide and 1 mol-% cross-linking agent to a water solution. The swelling of the polymer, i.e. the swelling of the thermo-reversible superabsorbent in the water solution, is measured in volume/gram dry superabsorbent from the temperature 27° C. to the temperature 37° C. Accordingly, the thermo-reversible superabsorbent exhibits a lower swelling in the higher temperature interval from 32 to 37° C., and a higher swelling in the lower temperature interval from 27° C. to 31° C. This change of the inclination to swell, i.e. the liquid absorption capacity, is valid for both a temperature reduction and a temperature increase.

The invention is primarily intended for diapers or incontinence protectors which are to be used during a prolonged period of time, for example during the night, when wetting often takes place on several occasions. However, the invention is of course also applicable on other types of diapers, incontinence protectors, sanitary napkins or the like.

The invention should not be regarded as being limited to the herein described embodiments, but a number of further variants and modifications are conceivable within the scope of the following claims.

What is claimed is:

1. An absorbent structure for use in an absorbent article, comprising:
   two end portions;
   a crotch portion located between said end portions; and
   superabsorbent material having a thermo-reversible liquid absorption capacity;
   wherein said superabsorbent material having a thermo-reversible liquid absorption capacity is located in one or several delimited areas in the absorbent structure, wherein at least one of said delimited areas is arranged in direct contact with an area of the absorbent structure which is free from said superabsorbent material having a thermo-reversible liquid absorption capacity, and the structure also comprises superabsorbent material without a thermo-reversible liquid absorption capacity, wherein the superabsorbent material without a thermo-reversible liquid absorption capacity is located primarily in the end portions of the structure.

2. The absorbent structure according to claim 1, wherein the superabsorbent material having a thermo-reversible liquid absorption capacity is located primarily in the crotch portion of the structure.

3. The absorbent structure according to claim 1, wherein the superabsorbent material having a thermo-reversible liquid absorption capacity is a thermo-reversible polymer having a cloud point, $C_p$, within the temperature interval 30–37° C.

4. The absorbent structure according to claim 1, wherein the liquid absorption capacity of the superabsorbent material having a thermo-reversible liquid absorption capacity is lower at a temperature above 32–35° C. than the liquid absorption capacity at a temperature below 32–35° C.

5. The absorbent structure according to claim 1, wherein the superabsorbent material having a thermo-reversible liquid absorption capacity is a thermo-reversible polymer having a cloud point, $C_p$, within the temperature interval 32–35° C., wherein the liquid absorption capacity of the polymer changes at the cloud point.

6. The absorbent structure according to claim 1, wherein a portion of superabsorbent material having a thermo-reversible liquid absorption capacity is at least 5% of the total weight of the absorbent structure in the crotch portion.

7. The absorbent structure according to claim 1, wherein the superabsorbent material having a thermo-reversible liquid absorption capacity is constituted by a cross-linked polymer of N-isopropylacrylamide.

8. The absorbent structure according to claim 1, wherein the superabsorbent material having a thermo-reversible liquid absorption capacity is constituted by a cross-linked co-polymer containing N-isopropylacrylamide and vinyl monomer containing carboxylic acid.

9. The absorbent structure according to claim 1, wherein vinyl monomer containing carboxylic acid is constituted by acrylic acid.

10. The absorbent structure according to claim 1, wherein the superabsorbent material having a thermo-reversible liquid absorption capacity is constituted by a cross-linked copolymer containing N-isopropylacrylamide and monomer containing sulfonic acid.

11. The absorbent structure according to claim 1, wherein the superabsorbent material having a thermo-reversible liquid absorption capacity is constituted by ethylhydroxyethyl cellulose.

12. The absorbent structure according to claim 1, wherein the absorbent structure exhibits a first and a second layer, wherein the second layer exhibits a higher density than the first layer.

13. An absorbent article comprising:
   a liquid-permeable cover layer;
   a liquid-impervious cover layer;
   an absorbent structure enclosed between the cover layers, which structure exhibits two end portions and a crotch portion located there between;

wherein a superabsorbent material having a thermo-reversible liquid absorption capacity is located primarily in the crotch portion of the absorbent structure, and the structure also comprises superabsorbent material without a thermo-reversible liquid absorption capacity, wherein the superabsorbent material without a thermo-reversible liquid absorption capacity is located primarily in the end portions of the structure.

14. The absorbent structure according to claim 13, wherein the superabsorbent material having a thermo-reversible liquid absorption capacity is located primarily in a part of the crotch portion of the absorbent structure which is located closest to the liquid-permeable cover layer.

15. The absorbent article according to claim 14 and further exhibiting an absorbent structure which at least comprises a liquid receiving layer located closer to the liquid-permeable cover layer, and a liquid storage layer located nearer to the liquid-impervious cover layer, wherein the superabsorbent material having a thermo-reversible liquid absorption capacity is located primarily in the liquid receiving layer of the absorbent structure.

* * * * *